United States Patent [19]

Crounse et al.

[11] 4,096,176
[45] Jun. 20, 1978

[54] BENZOYLBENZOIC ACIDS

[75] Inventors: Nathan N. Crounse, Cincinnati; Paul J. Schmidt, Sharonville, both of Ohio

[73] Assignee: Sterling Drug Inc., New York, N.Y.

[21] Appl. No.: 314,443

[22] Filed: Dec. 12, 1972

[51] Int. Cl.² .............................................. C07C 65/20
[52] U.S. Cl. ............................... 260/517; 260/293.58; 260/293.79; 260/287 P; 260/326.34; 260/326.47
[58] Field of Search ........................................ 260/517

[56]         References Cited
        U.S. PATENT DOCUMENTS

| | | | |
|---|---|---|---|
| 1,663,229 | 3/1928 | Adams et al. | 260/517 |
| 1,762,978 | 6/1930 | Gubelmann et al. | 260/517 |
| 3,131,178 | 4/1964 | Archer et al. | 260/517 |
| 3,491,112 | 1/1970 | Lin | 260/517 |
| 3,646,011 | 2/1972 | Archer et al. | 260/517 |

FOREIGN PATENT DOCUMENTS 645,999   7/1928   France.

OTHER PUBLICATIONS

Allais Chem. Abstracts, vol. 42 (1948), pp. 4998–4999.

*Primary Examiner*—Anton H. Sutto
*Attorney, Agent, or Firm*—Theodore C. Miller; B. Woodrow Wyatt

[57]            ABSTRACT

Substituted 3,3-diphenylphthalides, useful as color precursors, particularly in the art of pressure-sensitive duplicating systems, are prepared by condensing substituted 2-benzoylbenzoic acids with substituted anilines.

3 Claims, No Drawings

BENZOYLBENZOIC ACIDS

This invention relates to substituted 3,3-diphenylphthalides useful as color precursors, to substituted 2-benzoylbenzoic acids useful as intermediates in preparing said substituted 3,3-diphenylphthalides and to processes for preparing said substituted 3,3-diphenylphthalides.

In its substituted 3,3-diphenylphthalide aspect the invention provides 3-(2-X-4-X-phenyl)-3-(2-$Y^2$-4-$Y^4$-phenyl)-4-$Z^4$-5-$Z^5$-6-$Z^6$-7-$Z^7$-phthalide of the formula

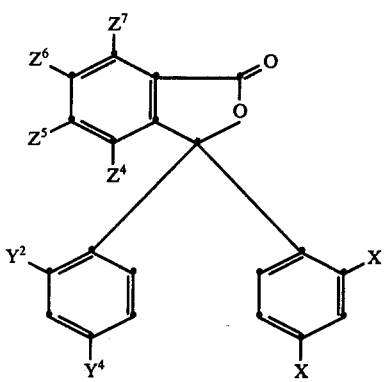

Formula I wherein:

X is dialkylamino wherein alkyl is non-tertiary alkyl of one to four carbon atoms;

$Y^2$ is hydrogen, non-tertiary alkyl of one to four carbon atoms, dialkylamino wherein alkyl is non-tertiary alkyl of one to four carbon atoms, alkanoylamino of two to five carbon atoms or non-tertiary alkoxy of one to four carbon atoms;

$Y^4$ is the same as $Y^2$ when $Y^2$ is dialkylamino, or dialkylamino wherein alkyl is non-tertiary alkyl of one to four carbon atoms, pyrrolidino, piperidino or alkyl(Q—(CH$_2$)$_n$)amino, wherein alkyl is non-tertiary alkyl of one to four carbon atoms, Q is hydroxy or chloro and $n$ is two to four when $Y^2$ is other than dialkylamino;

$Z^4$ is hydrogen or halo;

$Z^5$ is the same as $Z^4$; or non-tertiary alkyl of one to four carbon atoms, nitro, amino, dialkylamino wherein alkyl is non-tertiary alkyl of one to four carbon atoms or halo when $Z^4$, $Z^6$ and $Z^7$ are each hydrogen;

$Z^6$ is the same as $Z^4$; or non-tertiary alkyl of one to four carbon atoms, nitro, amino, dialkylamino wherein alkyl is non-tertiary alkyl of one to four carbon atoms or halo when $Z^4$, $Z^5$ and $Z^7$ are each hydrogen; and $Z^7$ is the same as $Z^4$.

The compounds of Formula I are useful as color precursors, particularly in the art of presure-sensitive duplicating systems.

In its substituted 2-benzoylbenzoic acid aspect the invention provides 2-(2-$Y'^2$-4-$Y'^4$-benzoyl)-3-$Z^4$-4-$Z'^5$-5-$Z'^6$-6-$Z^7$-benzoic acid of the formula Formula II $$\begin{array}{c} \text{structure} \end{array}$$

wherein:

$Y'^2$ is dialkylamino wherein alkyl is non-tertiary alkyl of one to four carbon atoms, alkanoylamino of two to five carbon atoms, or non-tertiary alkoxy of one to four carbon atoms; $Y'^4$ is the same as $Y'^2$ when $Y'^2$ is dialkylamino; or dialkylamino wherein alkyl is non-tertiary alkyl of one to four carbon atoms, pyrrolidino, piperidino or alkyl(Q'—(CH$_2$)$_n$)amino, wherein alkyl is non-tertiary alkyl of one to four carbon atoms, Q' is chloro and $n$ is two to four when $Y'^2$ is other than dialkylamino;

$Z^4$ is hydrogen or halo;

$Z'^5$ is the same as $Z^4$; or dialkylamino wherein alkyl is non-tertiary alkyl of one to four carbon atoms when $Z^4$, $Z'^6$ and $Z^7$ are each hydrogen;

$Z'^6$ is the same as $Z^4$; or dialkylamino wherein alkyl is non-tertiary alkyl of one to four carbon atoms when $Z^4$, $Z'^5$ and $Z^7$ are each hydrogen;

$Z^7$ is the same as $Z^4$ and acid addition salts thereof.

The compounds of Formula II are useful as intermediates in the following processes for preparing compounds of Formula I.

In one of its process aspects the invention provides the process for preparing 3-(2-X-4-X-phenyl)-3-(2-$Y^2$-4-$Y'^4$-phenyl)-4-$Z^4$-5-$Z'''^5$-6-$Z''^6$-7-$Z^7$-phthalide of the formula

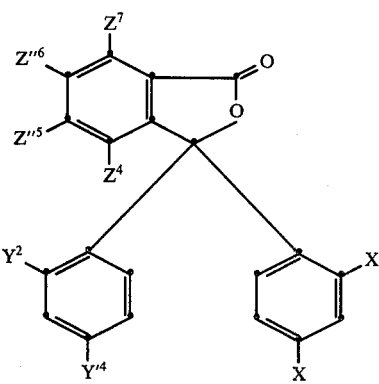

Formula III which comprises condensing 2-(2-$Y'^2$-4-$Y'^4$-benzoyl)-3-$Z^4$-4-$Z'''^5$-5-$Z''^6$-6-$Z^7$-benzoic acid of the formula

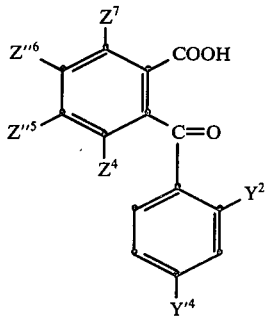

Formula IV with 1-X-3-X-benzene of the formula

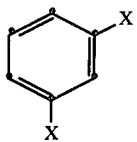

Formula V in contact with the anhydride of an alkanoic acid of two to five carbon atoms, phosphorus oxychloride or thionyl chloride, wherein:

X is dialkylamino wherein alkyl is non-tertiary alkyl of one to four carbon atoms;

$Y^2$ is hydrogen, non-tertiary alkyl of one to four carbon atoms, dialkylamino wherein alkyl is non-tertiary alkyl of one to four carbon atoms, alkanoylamino of two to five carbon atoms or non-tertiary alkoxy of one to four carbon atoms;

$Y'^4$ is the same as $Y^2$ when $Y^2$ is dialkylamino; or dialkylamino wherein alkyl is non-tertiary alkyl of one to four carbon atoms, pyrrolidino, piperidino or alkyl(Q'—(CH$_2$)$_n$)amino, wherein alkyl is non-tertiary alkyl of one to four carbon atoms, Q' is chloro and $n$ is two to four when $Y^2$ is other than dialkylamino;

$Z^4$ is hydrogen or halo;

$Z'''^5$ is the same as $Z^4$; or non-tertiary alkyl of one to four carbon atoms, nitro, dialkylamino wherein alkyl is non-tertiary alkyl of one to four carbon atoms or halo when $Z^4$, $Z'''^6$ and $Z^7$ are each hydrogen;

$Z'''^6$ is the same as $Z^4$; or non-tertiary alkyl of one to four carbon atoms, nitro, dialkylamino wherein alkyl is non-tertiary alkyl of one to four carbon atoms or halo when $Z^4$, $Z'''^5$ and $Z^7$ are each hydrogen; and $Z^7$ is the same as $Z^4$.

In its other process aspect the invention provides the process for preparing 3-(2-X-4-X-phenyl)-3-(2-$Y^2$-4-$Y'^4$-phenyl)-4-$Z^4$-5-$Z'''^5$-6-$Z'''^6$-7-$Z^7$-phthalide of Formula III which comprises condensing 2-(2-X-4-X-benzoyl)-3-$Z^4$-4-$Z'''^5$-5-$Z'''^6$-6-$Z^7$-benzoic acid of the formula

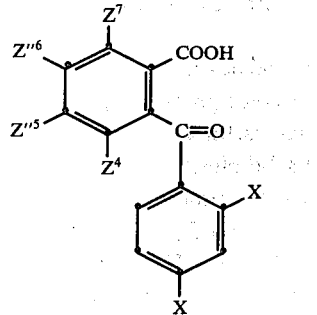

Formula VI with 1-$Y^2$-3-$Y''^4$-benzene of the formula

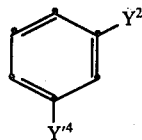

Formula VII in contact with the anhydride of an alkanoic acid of two to five carbon atoms, phosphorus oxychloride or thionyl chloride, wherein:

X is dialkylamino wherein alkyl is non-tertiary alkyl of one to four carbon atoms;

$Y^2$ is hydrogen, non-tertiary alkyl of one to four carbon atoms, dialkylamino wherein alkyl is non-tertiary alkyl of one to four carbon atoms, alkanoylamino of two to five carbon atoms or non-tertiary alkoxy of one to four carbon atoms;

$Y'^4$ is the same as $Y^2$ when $Y^2$ is dialkylamino; or dialkylamino wherein alkyl is non-tertiary alkyl of one to four carbon atoms, pyrrolidino, piperidino or alkyl(Q'—(CH$_2$)$_n$)amino, wherein alkyl is non-tertiary alkyl of one to four carbon atoms, Q' is chloro and $n$ is two to four when $Y^2$ is other than dialkylamino;

$Z^4$ is hydrogen or halo;

$Z'''^5$ is the same as $Z^4$; or non-tertiary alkyl of one to four carbon atoms, nitro, dialkylamino wherein alkyl is non-tertiary alkyl of one to four carbon atoms or halo when $Z^4$, $Z'''^6$ and $Z^7$ are each hydrogen;

$Z'''^6$ is the same as $Z^4$; or non-tertiary alkyl of one to four carbon atoms, nitro, dialkylamino wherein alkyl is non-tertiary alkyl of one to four carbon atoms or halo when $Z^4$, $Z'''^5$ and $Z^7$ are each hydrogen; and $Z^7$ is the same as $Z^4$.

The foregoing two process aspects of the invention do not provide directly the compounds of Formula I wherein $Y^4$ is alkyl(Q—(CH$_2$)$_n$)amino wherein Q is hydroxy. However, such compounds are provided by carrying out either of the process aspects of the invention with the appropriate intermediates wherein Q is hydroxy and the anhydride of an alkanoic acid of two to five carbon atoms as the condensing agent, and dealkanoylating the resulting product wherein Q is the corresponding alkanoyloxy of two to five carbon atoms.

Nor do the foregoing two process aspects of the invention provide directly the compounds of Formula I wherein $Z^5$ or $Z^6$ is amino. However, such compounds are provided by carrying out either of the process aspects of the invention with the appropriate intermediates wherein $Z^5$ or $Z^6$ is amino and, if the anhydride of an alkanoic acid of two to five carbon atoms is used as the condensing agent, dealkanoylating the resulting product wherein $Z^5$ or $Z^6$ is the corresponding alkanoylamino of two to five carbon atoms.

The generic terms used to define the invention will now be defined.

Non-tertiary alkyl of one to four carbon atoms is methyl, ethyl, propyl, isopropyl, butyl, isobutyl or sec-butyl.

Alkanoylamino of two to five carbon atoms is acetamido propionamido, butyrylamino, isobutyrylamino, valerylamino, isovalerylamino, α-methylbutyrylamino or pivaloylamino.

Non-tertiary alkoxy of one to four carbon atoms is methoxy, ethoxy, propoxy, isopropoxy, butoxy, isobutoxy or sec-butoxy.

Halo is fluoro, chloro, bromo or iodo.

The anhydrides of alkanoic acids of two to five carbon atoms are acetic anhydride, propionic anhydride, butyric anhydride, isobutyric anhydride, valeric anhydride, isovaleric anhydride, α-methylbutyric anhydride and pivalic anhydride.

The manner and process of making and using the invention and the best mode of carrying it out will now be described so as to enable any person skilled in the art to which it pertains to make and use it.

In carrying out the processes of the invention a mixture of 2-(2-$Y^2$-4-$Y'^4$-benzoyl)-3-$Z^4$-4-$Z'''^5$-5-$Z''^6$-6-$Z^7$-benzoic acid of Formula IV and 1-X-3-X-benzene of Formula V or a mixture of 2-(2-X-4-X-benzoyl)-3-$Z^4$-4-$Z'''^5$-5-$Z''^6$-6-$Z^7$-benzoic acid of Formula VI and 1-$Y^2$-3-$Y'^4$-benzene of Formula VII and the anhydride of an alkanoic anhydride, preferably acetic anhydride, phosphorus oxychloride or thionyl chloride with or without an inert diluent, is heated at a temperature in the range of 30°–150° C. In some cases the product of Formula III precipitates from the resulting mixture and may be isolated directly. Otherwise the resulting mixture is first acidified with a dilute aqueous mineral acid, for example, hydrochloric acid, and then basified, for example, with dilute aqueous sodium hydroxide, and the product is then isolated.

The compounds of Formula I wherein $Z^5$ or $Z^6$ is amino are alternatively provided by reduction of the corresponding compounds of Formula I wherein $Z^5$ or $Z^6$ is nitro with, for example, stannous chloride.

The compounds of Formula I wherein $Z^5$ or $Z^6$ is nitro are alternatively provided by nitration of the corresponding compounds of Formula I wherein $Z^5$ and $Z^6$ are hydrogen with, for example, a mixture of nitric acid and sulfuric acid. The nitration can produce the 5-nitro isomer, the 6-nitro isomer or a mixture of both.

The compounds of Formula I wherein $Z^5$ or $Z^6$ is halo are alternatively provided by halogenation of the diazonium salts derived from the corresponding compounds of Formula I wherein $Z^5$ or $Z^6$ is amino with, for example, fluoroboric acid, cuprous chloride, cuprous bromide or potassium iodide.

As stated above the compounds of Formula I are useful as color precursors, particularly in the art of pressure-sensitive duplicating systems. Like other color precursors in current use in this art the compounds of Formula I are colorless under neutral or basic conditions, but become colored when contacted with an acidic material such as silica gel, a phenolic resin or an acidic clay. It is sometimes desired that the images produced by such color precursors be copiable by xerographic means. A widely used diphenylphthalide color precursor is crystal violet lactone of the formula

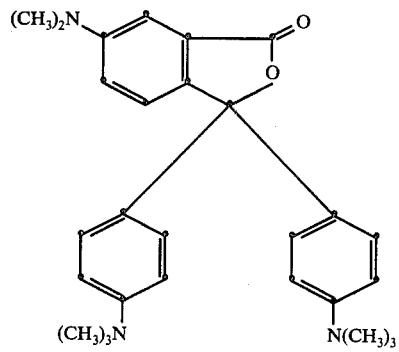

Crystal violet lactone produces a blue image which has the advantage of being intense but which suffers the disadvantage of being poorly copiable by xerographic means. To counteract this disadvantage other color precursors have been mixed with crystal violet lactone as described, for example, in U.S. Pat. No. 3,525,630. The images produced by the compounds of Formula I, although generally less intense in color than the images produced by crystal violet lactone, are readily copiable by xerographic means. For this reason the difficulties inherent in using mixed color precursors to achieve xerographic copiability can be avoided by using a compound Formula I alone.

The compounds of Formula IV and Formula VI, which include among them the compounds of Formula II, are prepared by condensing the corresponding 3-$Z^4$-4-$Z'''^5$-5-$Z''^6$-6-$Z^7$-phthalic anhydrides of the formula

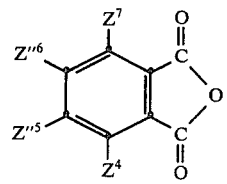

Formula VIII with the corresponding 1-$Y^2$-3-$Y'^4$-benzenes of Formula VII or 1-X-3-X-benzenes of Formula V, respectively, in contact with a Lewis acid, for example, aluminum chloride or zinc chloride, and with a diluent, for example, benzene, chlorobenzene or o-dichlorobenzene, at a temperature in the range of 20°–200° C. This condensation can produce isomers or mixtures of isomers when the $Z'''^5$ or $Z''^6$ substituent of the compounds of Formula VIII is alkyl, nitro, dialkylamino or halo. Thus the derived compounds of Formula IV and Formula VI have the substituent at the 4-position or the 5-position. Compounds of Formula IV or Formula VI having the substituent in the 4-position or the 5-position produce the corresponding compounds of Formula I having the substituent in the 5-position or the 6-position.

Acid addition salts of the compounds of Formula II, Formula IV and Formula VI can be prepared with inorganic (mineral) or organic acids. If inorganic, the acid can be, for example, hydrochloric acid, hydrobromic acid, nitric acid, phosphoric acid, sulfuric acid or sulfamic acid. If organic, the acid can be, for example, acetic acid, glycolic acid, lactic acid, quinic acid, hydrocinnamic acid, succinic acid, tartaric acid, citric acid, methanesulfonic acid or benzenesulfonic acid.

The molecular structures of the compounds of Formula I, Formula II, Formula IV and Formula VI follow from the structures of the compounds of Formula V, Formula VII and Formula VIII and the synthetic method and may be identified and corroborated by observation of one or more of the following physical properties: color, melting point (m.p.), solubility behavior, acid-base behavior, thin layer chromatographic spectrum, infrared spectrum, mass spectrum, nuclear magnetic resonance spectrum and ultraviolet spectrum.

The compounds of Formula VIII wherein $Z^4$ is halo and $Z'''^5$ or $Z'''^6$ is nitro or halo are known. Some of the compounds of Formula VIII wherein $Z'''^5$ or $Z'''^6$ is dialkylamino are also known. Those which are not known can be prepared, for example, according to the method of U.S. Pat. No. 2,597,965 starting with diethyl 4-aminophthalate and, successively, appropriately N-alkylating, de-ethylating and cyclizing.

Some of the compounds of Formula V and the compounds of Formula VII wherein $Y^2$ is dialkylamino are known. Those which are not known can be prepared, for example, by appropriately N-alkylating m-phenylenediamine.

Some of the compounds of Formula VII wherein $Y^2$ is hydrogen are known. Those which are not known can be prepared by appropriately N-alkylating aniline.

Some of the compounds of Formula VII wherein $Y^2$ is alkyl are known. Those which are not known can be prepared, for example, starting with the appropriate alkylbenzene and, successively, 4-nitrating, reducing the nitro to amino, N-acetylating, 3-nitrating, deacetylating, deaminating, reducing the nitro to amino and appropriately N-alkylating.

Some of the compounds of Formula VII wherein $Y^2$ is alkanoylamino are known. Those which are not known can be prepared, for example, starting with m-nitroaniline and, successively, N-alkanoylating, reducing the nitro to amino and appropriately N-alkylating.

Some of the compounds of Formula VII wherein $Y^2$ is alkoxy are known. Those which are not known can be prepared, for example, starting with m-hydroxyacetanilide and, successively, appropriately O-alkylating, deacetylating and appropriately N-alkylating.

The foregoing methods also provide the corresponding compounds of Formula VII wherein $Y'^4$ is alkyl(hydroxy-$(CH_2)_n$)amino which are not known.

The following examples illustrate the invention.

EXAMPLE 1

A. A mixture of phthalic anhydride (30 g.), N,N-dimethylaniline (60.5 g.), aluminum chloride (60 g.) and chlorobenzene (180 g.) was heated (to 75° C.) during one hour, then cooled. Ice (500 ml.) was added, the chlorobenzene layer was separated and the chlorobenzene was steam distilled. Addition of base to a solution of the residue in dilute sulfuric acid afforded 2-(4-(dimethylamino)benzoyl)benzoic acid (IV: $Y^2 = Z^4 = Z'''^5 = Z'''^6 = Z^7 = H$, $Y'^4 = (CH_3)_2N$).

B. A mixture of 2-(4-(dimethylamino)benzoyl)benzoic acid (26.8 g.), N,N,N',N'-tetramethyl-m-phenylenediamine (16.4 g.) and acetic anhydride (80 g.) was heated (to 95° C.) during one hour, cooled and poured into dilute hydrochloric acid. The resulting mixture was basified. Recrystallization of the resulting solid from a mixture of toluene and hexane afforded 3-(2,4-bis(dimethylamino)phenyl)-3-(4-(dimethylamino)phenyl)phthalide (I: $X = Y^4 = (CH_3)_2N$, $Y^2 = Z^4 = Z^5 = Z^6 = Z^7 = H$) (m.p. 190°-194° C.).

When applied to acidic clay 3-(2,4-bis(dimethylamino)phenyl)-3-(4-(dimethylamino)phenyl)phthalide formed a gray-black image which was xerographically copiable.

C. Substituting N,N,N',N'-tetra(sec-butyl)-m-phenylenediamine (prepared by N-alkylating m-phenylenediamine with sec-butyl bromide) for N,N,N',N'-tetramethyl-m-phenylenediamine in part B of this example, there is obtained 3-(2,4-bis(di-sec-butylamino)phenyl)-3-(4-(dimethylamino)phenyl)phthalide (I: $X = (CH_3CH_2(CH_3)CH)_2N$, $Y^2 = Z^4 = Z^5 = Z^6 = Z^7 = H$, $Y^4 = (CH_3)_2N$).

EXAMPLE 2

A. In a manner similar to that of part A of Example 1 condensation of phthalic anhydride (60 g.) and N,N-diethyl-m-toluidine (162.8 g.) in contact with aluminum chloride (120 g.) and with chlorobenzene (360 ml.) as diluent afforded 2-(2-methyl-4-(diethylamino)benzoyl)benzoic acid (IV: $Y^2 = CH_3$, $Y'^4 = (CH_3CH_2)_2N$, $Z^4 = Z'''^5 = Z'''^6 = Z^7 = H$).

B. In a manner similar to that of part B of Example 1 condensation of 2-(2-methyl-4-(diethylamino)benzoyl)benzoic acid (25 g.) and N,N,N',N'-tetramethyl-m-phenylenediamine (13.2 g.) in contact with acetic anhydride (75 g.) and recrystallization of the resulting product afforded 3-(2,4-bis(dimethylamino)phenyl)-3-(2-methyl-4-(diethylamino)phenyl)phthalide (I: $X = (CH_3)_2N$, $Y^2 = CH_3$, $Y^4 = (CH_3CH_2)_2N$, $Z^4 = Z^5 = Z^6 = Z^7 = H$) in a first crop from toluene (m.p. 204°-206° C.) and in a second crop from a mixture of toluene and hexane (m.p. 191°-195° C.).

When applied to acidic clay 3-(2,4-bis(dimethylamino)phenyl)-3-(2-methyl-4-(diethylamino)phenyl)phthalide formed a violet-gray image which was xerographically copiable.

C. Substituting m-butyl-N,N-dimethylaniline (prepared by N-methylating m-butylaniline with dimethyl sulfate) for N,N-diethyl-m-toluidine in part A of this example, there is obtained 2-(2-butyl-4-(dimethylamino)benzoyl)benzoic acid (IV: $Y^2 = CH_3CH_2CH_2CH_2$, $Y'^4 = (CH_3)_2N$, $Z^4 = Z'''^5 = Z'''^6 = Z^7 = H$).

D. Substituting 2-(2-butyl-4-(dimethylamino)benzoyl)benzoic acid for 2-(2-methyl-4-(diethylamino)benzoyl)benzoic acid in part B of this example, there is obtained 3-(2,4-bis(dimethylamino)phenyl)-3,(2-butyl-4-(dimethylamino)phenyl)phthalide (I: $X = Y^4 = (CH_3)_2N$, $Y^2 = CH_3CH_2CH_2CH_2$, $Z^4 = Z^5 = Z^6 = Z^7 = H$).

EXAMPLE 3

A. A mixture of phthalic anhydride (5.92 g.), N,N,N',N'-tetramethyl-m-phenylenediamine (6.56 g.), zinc chloride (5.40 g.) and chlorobenzene (70 ml.) was heated under reflux for 3 hours. The chlorobenzene was decanted and the residue was air-dried. A solution of the residue in dilute hydrochloric acid (10%, 20 ml. plus 20 ml. of water) was diluted with more water (20 ml.), affording 2-(2,4-bis(dimethylamino)benzoyl)benzoic acid (II: $Y'^2 = Y'^4 = (CH_3)_2N$, $Z^4 = Z'^5 = Z'^6 = Z^7 = H$) dihydrochloride trihydrate (4 g., m.p. 136°-141° C.; after recrystallization from ethanol, m.p. 140°-141° C.). In another preparation the free base (m.p. 165°-168° C.) was obtained under less acidic conditions (pH 4 -6).

B. A mixture of crude 2-(2,4-bis(dimethylamino)benzoyl)benzoic acid (7 g.), N,N,N',N'-tetramethyl-m-phenylenediamine (1.64 g.) and acetic anhydride was warmed (at 25°–35° C.) during 2 to 3 hours, then poured into dilute hydrochloric acid (10%). The resulting mixture was basified and filtered with a filter aid. The filter cake was extracted with hot toluene. Dilution of the toluene extract with hexane afforded 3,3-bis(2,4-bis(-dimethylamino)phenyl)phthalide (I: $X = Y^2 = Y^4 = (CH_3)_2N$, $Z^4 = Z^5 = Z^6 = Z^7 = H$) m.p. 186°–188° C.).

When applied to silica gel or standard field resin 3,3-bis(2,4-bis(dimethylamino)phenyl)phthalide formed a red-brown image which was xerographically copiable.

C. Substituting N,N,N',N'-tetra(sec-butyl)-m-phenylenediamine for N,N,N',N'-tetramethyl-m-phenylenediamine in part A of this example, there is obtained 2-(2,4-bis(di-sec-butylamino)benzoyl)benzoic acid (II: $Y'^2 = Y'^4 = (CH_3CH_2(CH_3)CH)_2N$, $Z^4 = Z'^5 = Z'^6 = Z^7 = H$).

D. Substituting N,N-diethyl-m-toluidine for N,N,N',N'-tetramethyl-m-phenylenediamine in part B of this example, there is obtained 3-(2,4-bis(dimethylamino)phenyl)-3-(2-methyl-4-(diethylamino)-phenyl)phthalide, the compound of part B of Example 2.

E. Substituting N-phenylpyrrolidine, N-phenylpiperidine or N-ethyl-N-(3-chloropropyl)aniline for N,N,N',N'-tetramethyl-m-phenylenediamine in part B of this example, there are obtained, respectively, 3-(2,4-bis(dimethylamino)phenyl)-3-(4-pyrrolidinophenyl)phthalide (I: $X = (CH_3)_2N$, $Y^2 = Z^4 = Z^5 = Z^6 = Z^7 = H$,

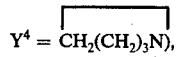
$Y^4 = CH_2(CH_2)_3N)$, 3-(2,4-bis(dimethylamino)phenyl)-3-(4-piperidinophenyl)phthalide (I: $X = (CH_3)_2N$, $Y^2 = Z^4 = Z^5 = Z^6 = Z^7 = H$,

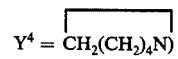
$Y^4 = CH_2(CH_2)_4N)$ and 3-(2,4-bis(dimethylamino)phenyl)-3-(4-(ethyl(3-chloropropyl)amino)phenyl)phthalide (I: $X = (CH_3)_2N$, $Y^2 = Z^4 = Z^5 = Z^6 = Z^7 = H$, $Y^4 = CH_3CH_2(Cl(CH_2)_2)N)$.

EXAMPLE 4

A. In a manner similar to that of part B of Example 3 condensation of 2-(2,4-bis(dimethylamino)benzoyl)benzoic acid (2.4 g.) and m-(dimethylamino)acetanilide (1.42 g.) and recrystallization of part of the product from a mixture of toluene, ligroin and hexane and part from a mixture of ethyl acetate and hexane afforded 3-(2,4-bis(dimethylamino)phenyl)-3-(2-acetamido-4-(dimethylamino)phenyl)phthalide (I: $X = Y^4 = (CH_3)_2N$, $Y^2 = CH_3CONH$, $Z^4 = Z^5 = Z^6 = Z^7 = H$) (m.p. 97°–136° C.).

When applied to standard field resin 3-(2,4-bis(dimethylamino)phenyl)-3-(2-acetamido-4-(dimethylamino)phenyl)phthalide formed a red-blue-brown image which was xerographically copiable.

B. Substituting m-(dimethylamino)-2,2-dimethylpropionanilide (prepared by N-alkanoylating N,N-dimethylphenylenediamine with pivaloyl chloride) for m-(dimethylamino)acetanilide in part A of this example, there is obtained 3-(2,4-bis(dimethylamino)phenyl)-3-(2-pivaloylamino-4-(dimethylamino)phenyl)phthalide (I: $X = Y^4 = (CH_3)_2N$, $Y^2 = (CH_3)_3CCONH$, $Z^4 = Z^5 = Z^6 = Z^7 = H$).

C. Condensation of phthalic anhydride and m-(dimethylamino)acetanilide by the method of part A of Example 1 affords 2-(2-acetamido-4-(dimethylamino)benzoyl)benzoic acid (II: $Y'^2 = CH_3CONH$, $Y'^4 = (CH_3)_2N$, $Z^4 = Z'^5 = Z'^6 = Z^7 = H$).

D. Condensation of 2-(2-acetamido-4-(dimethylamino)benzoyl)benzoic acid and N,N,N',N'-tetramethyl-m-phenylenediamine by the method of part B of Example 1 affords 3-(2,4-bis(dimethylamino)phenyl)-3-(2-acetamido-4-(dimethylamino)phenyl)phthalide, the compound of part A of this example.

EXAMPLE 5

A. In a manner similar to that of part A of Example 1 condensation of phthalic anhydride (15 g.) and m-ethoxy-N,N-diethylaniline (19 g.) in contact with aluminum chloride (15 g.) and with o-dichlorobenzene as diluent afforded 2-(2-ethoxy-4-(diethylamino)benzoyl)benzoic acid (II: $Y'^2 = CH_3CH_2O$, $Y'^4 = (CH_3CH_2)_2N$, $Z^4 = Z'^4 = Z'^6 = Z^7 = H$) (11 g., m.p. 174°–181° C.).

B. A mixture of 2-(2-ethoxy-4-(diethylamino)benzoyl)benzoic acid (6.82 g.), N,N,N',N'-tetramethyl-m-phenylenediamine (2.80 g.) and acetic anhydride (20 g.) was heated (70°–75° C.) during one hour, let stand overnight and poured into dilute hydrochloric acid. The resulting mixture was basified. Recrystallization of the resulting red precipitate from hexane followed by slurrying in alkaline water afforded 3-(2,4-bis(dimethylamino)phenyl)-3-(2-ethoxy-4-(diethylamino)phenyl)phthalide (I: $X = (CH_3)_2N$, $Y^2 = CH_3CH_2O$, $Y^4 = (CH_3CH_2)_2N$, $Z^4 = Z^5 = Z^6 = Z^7 = H$) (m.p. 146°–150° C.).

When applied to acidic clay 3-(2,4-bis(dimethylamino)phenyl)-3-(2-ethoxy-4-(diethylamino)phenyl)phthalide formed a blue-black image which was xerographically copiable.

C. Substituting m-isobutoxy-N,N-dimethylaniline (prepared by O-alkylating m-hydroxyacetanilide with isobutyl bromide, then deacetylating the resulting m-isobutoxyacetanilide, then N-alkylating the resulting m-isobutoxyaniline with methyl sulfate) for m-ethoxy-N,N-diethylaniline in part A of this example, there is obtained 2-(2-isobutoxy-4-(dimethylamino)benzoyl)benzoic acid (II: $Y'^2 = (CH_3)_2CHCH_2O$, $Y'^4 = (CH_3)_2N$, $Z^4 = Z'^5 = Z'^6 = Z^7 = H$).

D. Substituting 2-(2-isobutoxy-4-(dimethylamino)benzoyl)benzoic acid for 2-(2-ethoxy-4-(diethylamino)benzoyl)benzoic acid in part B of this example, there is obtained 3-(2,4-bis(dimethylamino)phenyl)-3-(2-isobutoxy-4-(dimethylamino)phenyl)phthalide (I: $X = (CH_3)_2N$, $Y^2 = (CH_3)_2CHCH_2O$, $Y^4 = (CH_3)_2N$, $Z^4 = Z^5 = Z^6 = Z^7 = H$).

E. Condensation of phthalic anhydride and N-(m-anisyl)pyrrolidine (prepared from m-anisidine and 1,4-dibromobutane), N-(m-anisyl)piperidine (prepared from m-anisidine and 1,5-dibromopentane) or N-methyl-N-(2-chloroethyl)-m-anisidine (prepared from N-methyl-m-anisine and 1-bromo-2-chloroethane) by the method of part A of Example 1 affords, respectively, 2-(2-methoxy-4-pyrrolidinobenzoyl)benzoic acid (II: $Y'^2 = CH_3O$, $Y'^4 =$

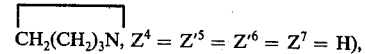
$CH_2(CH_2)_3N$, $Z^4 = Z'^5 = Z'^6 = Z^7 = H$), 2-(2-methoxy-4-piperidinobenzoyl)benzoic acid (II: $Y'^2 = CH_3O$, $Y'^4 =$ 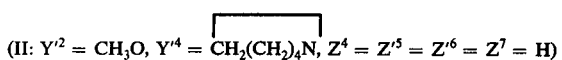 $CH_2(CH_2)_4N$, $Z^4 = Z'^5 = Z'^6 = Z'^7 = H$)

and 2-(2-methoxy-4-(methyl(2-chloroethyl)amino)benzoyl)benzoic acid (II: $Y'^2 = CH_3O$, $Y'^4 = CH_3(ClCH_2CH_2)N$, $Z^4 = Z'^5 = Z'^6 = Z'^7 = H$).

F. Condensation of 2-(2-methoxy-4-pyrrolidinobenzoyl)benzoic acid, 2-(2-methoxy-4-piperidinobenzoyl)benzoic acid or 2-(2-methoxy-4-(methyl(2-chloroethyl)amino)benzoyl)benzoic acid with N,N,N',N'-tetramethyl-m-phenylenediamine by the method of part B of Example 1 affords, respectively, 3-(2,4-bis(dimethylamino)phenyl)-3-(2-methoxy-4-pyrrolidinophenyl)phthalide (I: $X = (CH_3)_2N$, $Y^2 = CH_3O$, $Y^4 =$ 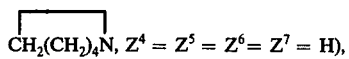 $CH_2(CH_2)_4N$, $Z^4 = Z^5 = Z^6 = Z^7 = H$), 3-(2,4-bis(dimethylamino)phenyl)-3-(2-methoxy-4-piperidinophenyl)phthalide (I: $X = (CH_3)_2N$, $Y^2 = CH_3O$, $Y^4 =$  $CH_2(CH_2)_4N$, $Z^4 = Z^5 = Z^6 = Z^7 = H$)

and 3-(2,4-bis(dimethylamino)phenyl)-3-(2-methoxy-4-(methyl(2-chloroethyl)amino)phenyl)phthalide (I: $X = (CH_3)_2N$, $Y^2 = {}^{CH_3}O$, $Y^4 = CH_3(ClCH_2CH_2)N$, $Z^4 = Z^5 = Z^6 = Z^7 = H$).

EXAMPLE 6

A. In a manner similar to that of part A of Example 1 condensation of tetrachlorophthalic anhydride (21.4 g.) and N,N-diethyl-m-toluidine (41 g.) in contact with aluminum chloride (30 g.) and with o-dichlorobenzene (90 ml.) as diluent afforded 2-(2-methyl-4-(diethylamino)benzoyl)-3,4,5,6-tetrachlorobenzoic acid (IV: $Y^2 = CH_3$, $Y'^4 = (CH_3CH_2)_2N$, $Z^4 = Z'''^5 = Z'''^6 = Z^7 = Cl$) (26 g., m.p. 117° C. with sublimation).

B. In a manner similar to that of part B of Example 1 condensation of 2-(2-methyl-4-(diethylamino)benzoyl)-3,4,5,6-tetrachlorobenzoic acid (22.4 g.) and N,N,N',N'-tetramethyl-m-phenylenediamine (8.20 g.) in contact with acetic anhydride (75 g.) and recrystallization of the resulting product from toluene afforded 3-(2,4-bis(dimethylamino)phenyl)-3-(2-methyl-4-(diethylamino)phenyl)-4,5,6,7-tetrachlorophthalide (I: $X = (CH_3)_2N$, $Y^2 = CH_3$, $Y^4 = (CH_3CH_2)_2N$, $Z^4 = Z^5 = Z^6 = Z^7 = Cl$) (m.p. 236°-238° C.; after slurrying in acetone, 237°-239° C.).

When applied to acidic clay 3-(2,4-bis(dimethylamino)phenyl)-3-(2-methyl-4-(diethylamino)phenyl)-4,5,6,7-tetrachlorophthalide formed an image which was xerographically copiable.

EXAMPLE 7

A. In a manner similar to that of part A of Example 3 condensation of tetrachlorophthalic anhydride (1.92 g.) and N,N,N',N'-tetramethyl-m-phenylenediamine (1.64 g.) in contact with zinc chloride (1.35 g.) and with chlorobenzene (40-45 ml.) as diluent afforded 2-(2,4-bis(dimethylamino)benzoyl)-3,4,5,6-tetrachlorobenzoic acid (II: $Y'^2 = Y'^4 = (CH_3)_2N$, $Z^4 = Z'^5 = Z'^6 = Z^7 = Cl$) (m.p. 199°-201° C.).

B. A mixture of most of the 2-(2,4-bis(dimethylamino)benzoyl)-3,4,5,6-tetrachlorobenzoic acid from part A of this example, N,N,N',N'-tetramethyl-m-phenylenediamine (0.82 g. plus 0.4 g.) and acetic anhydride was heated under reflux. Concentration of a toluene extract of the resulting product gave a tar, which was slurried in hexane, affording 3,3-bis(2,4-bis(dimethylamino)phenyl-4,5,6,7-tetrachlorophthalide (I: $X = Y^2 = Y^4 = (CH_3)_2N$, $Z^4 = Z^5 = Z^6 = Z^7 = Cl$) (m.p. 195°-197° C.).

When applied to acidic clay 3,3-bis(2,4-bis(dimethylamino)phenyl)-4,5,6,7-tetrachlorophthalide formed a red-blue image which was xerographically copiable.

C. Substituting tetrafluorophthalic anhydride, tetrabromophthalic anhydride or tetraiodophthalic anhydride for tetrachlorophthalic anhydride in part A of this example, there are obtained, respectively, 2-(2,4-bis(dimethylamino)benzoyl)-3,4,5,6-tetrafluorobenzoic acid (II: $Y'^2 = Y'^4 = (CH_3)_2N$, $Z^4 = Z'^5 = Z'^6 = Z^7 = F$), 2-(2,4-bis(dimethylamino)benzoyl)-3,4,5,6-tetrabromobenzoic acid (II: $Y'^2 = Y'^4 = (CH_3)_2N$, $Z^4 = Z'^5 = Z'^6 = Z^7 = Br$) and 2-(2,4-bis(dimethylamino)benzoyl)-3,4,5,6-tetraiodobenzoic acid (II: $Y'^2 = Y'^4 = (CH_3)_2N$, $Z^4 = Z'^5 = Z'^6 = Z'^7 = I$).

D. Substituting 2-(2,4-bis(dimethylamino)benzoyl)-3,4,5,6-tetrafluorobenzoic acid, 2-(2,4-bis(dimethylamino)benzoyl)-3,4,5,6-tetrabromobenzoic acid or 2-(2,4-bis(dimethylamino)benzoyl)-3,4,5,6-tetraiodobenzoic acid for 2-(2,4-bis(dimethylamino)benzoyl)-3,4,5,6-tetrachlorobenzoic acid in part B of this example, there are obtained, respectively, 3,3-bis(2,4-bis(dimethylamino)phenyl)-4,5,6,7-tetrafluorophthalide (I: $X = Y^2 = Y^4 = (CH_3)_2N$, $Z^4 = Z^5 = Z^6 = Z^7 = F$), 3,3-bis(2,4-bis(dimethylamino)phenyl)-4,5,6,7-tetrabromophthalide (I: $X = Y^2 = Y^4 = (CH_3)_2N$, $Z^4 = Z^5 = Z^6 = Z^7 = Br$) and 3,3-bis(2,4-bis(dimethylamino)phenyl)-4,5,6,7-tetraiodophthalide (I: $X = Y^2 = Y^4 = (CH_3)_2N$, $Z^4 = Z^5 = Z^6 = Z^7 = I$).

EXAMPLE 8

Three portions of a mixture of concentrated nitric acid (0.6 ml. each portion) and concentrated sulfuric acid (0.66 ml. each portion) were added to a mixture of 3-(2,4-bis(dimethylamino)phenyl)-3-(4-(dimethylamino)phenyl)phthalide (4.17 g.) and concentrated sulfuric acid (20 ml.) with cooling. After each addition the temperature was allowed to rise to room temperature. The resulting mixture was poured onto ice and the resulting mixture was basified, affording 3-(2,4-bis(dimethylamino)phenyl)-3-(4-(dimethylamino)phenyl)-5 or 6-nitrophthalide (I: $X = Y^4 = (CH_3)_2N$, $Y^2 = Z^4 = Z^7 = H$, $Z^5$ or $Z^6 = O_2N$ and the other of $Z^5$ or $Z^6 = H$) or a mixture of both.

When applied to silica gel 3-(2,4-bis(dimethylamino)phenyl)-3-(4-(dimethylamino)phenyl)-5 or 6-nitrophthalide formed a gray-black image which was xerographically copiable.

EXAMPLE 9

In a manner similar to that of Example 8 nitration of 3-(2,4-bis(dimethylamino)phenyl)-3-(2-methyl-4-(diethylamino)phenyl)phthalide (4.57 g.) afforded 3-(2,4-bis(dimethylamino)phenyl)-3-(2-methyl-4-(diethylamino)phenyl)-5 or 6-nitrophthalide (I: $X = (CH_3)_2N$, $Y^2 = CH_3$, $Y^4 = (CH_3CH_2)_2N$, $Z^4 = Z^7 = H$, $Z^5$ or $Z^6 = O_2N$ and the other of $Z^5$ or $Z^6 = H$) or a mixture of both.

When applied to silica gel 3-(2,4-bis(dimethylamino)phenyl)-3-(2-methyl-4-(diethylamino)phenyl)-5 or 6-nitrophthalide formed a gray-black image which was xerographically copiable.

EXAMPLE 10

A. Stannous chloride dihydrate (6.7 g.) was added slowly to a mixture of most of the product of Example 8 and concentrated hydrochloric acid (50 ml.) with heating (60° C.). After one hour the resulting mixture was cooled, made alkaline and filtered, affording 3-(2,4-bis(dimethylamino)phenyl)-3-(4-(dimethylamino)phenyl)-5 or 6-aminophthalide (I: $X = Y^4 = (CH_3)_2N$, $Y^2 = Z^4 = Z^7 = H$, $Z^5$ or $Z^6 = H_2N$ and the other of $Z^5$ or $Z^6 = H$) or a mixture of both.

When applied to silica gel 3-(2,4-bis(dimethylamino)phenyl-3-(4-(dimethylamino)phenyl)-5 or 6-aminophthalide formed a gray-violet or gray-brown image which was xerographically copiable.

B. Condensation of 4-aminophthalic anhydride and N,N,N',N'-tetramethyl-m-phenylenediamine by the method of part A of Example 3 affords 2-(2,4-bis(dimethylamino)benzoyl)-5-aminobenzoic acid.

C. Condensation of 2-(2,4-bis(dimethylamino)benzoyl)-5-aminobenzoic acid and N,N,N',N'-tetramethyl-m-phenylenediamine by the method of part B of Example 3 and deacetylation of the resulting product affords 3,3-(2,4-bis(dimethylamino)phenyl)-6-aminophthalide (I: $X = Y^2 = Y^4 = (CH_3)_2N$, $Z^4 = Z^5 = Z^7 = H$, $Z^6 = H_2N$).

EXAMPLE 11

In a manner similar to that of Example 10 reduction of most of the product of Example 9 afforded 3-(2,4-bis(dimethylamino)phenyl)-3-(2-methyl-4-(diethylamino)phenyl)-5 or 6-aminophthalide (I: $X = (CH_3)_2N$, $Y^2 = CH_3$, $Y^4 = (CH_3CH_2)_2N$, $Z^4 = Z^7 = H$, $Z^5$ or $Z^6 = H_2N$ and the other of $Z^5$ or $Z^6 = H$) or a mixture of both.

When applied to silica gel 3-(2,4-bis(dimethylamino)phenyl)-3-(2-methyl-4-(diethylamino)phenyl)-5 or 6-aminophthalide formed a gray-violet or gray-black image which was xerographically copiable.

EXAMPLE 12

A. A mixture of 4-(dimethylamino)phthalic anhydride (7 g.), N,N-dimethylaniline (9.12 g.), aluminum chloride (11.7 g.) and benzene (36.5 ml.) was stirred (for 10 min.) at ice-bath temperature, then overnight at room temperature. The mixture was then extracted with dilute sulfuric acid (20%, 80 ml.). Adjustment of the pH of the acidic extract to 5 afforded a mixture of 2-(4-(dimethylamino)benzoyl)-4-(dimethylamino)benzoic acid (IV: $Y^2 = Z^4 = Z'''^6 = Z^7 = H$, $Y'^4 = Z'''^5 = (CH_3)_2N$) and 2-(4-(dimethylamino)benzoyl)-5-(dimethylamino)benzoic acid (IV: $Y^2 = Z^4 = Z'''^5 = Z^7 = H$, $Y'^4 = Z'''^6 = (CH_3)_2N$) (6.3 g.).

B. A mixture of part (3.12 g.) of the mixture of products from part A of this example, N,N,N',N'-tetramethyl-m-phenylenediamine (1.5 g.) and acetic anhydride (20 g.) was heated (to 85° C.), then cooled. The resulting precipitate was washed with ether, washed with alkali and recrystallized from acetone, affording 3-(2,4-bis(dimethylamino)phenyl)-3-(4-(dimethylamino)phenyl)-5-(dimethylamino)phthalide (I: $X = Y^4 = Z^5 = (CH_3)_2N$, $Y^2 = Z^4 = Z^6 = Z^7 = H$) (m.p. 222°–225° C.).

When applied to acidic clay 3-(2,4-bis(dimethylamino)phenyl)-3-(4-dimethylamino)phenyl)-5-(dimethylamino)phthalide slowly formed a blue-gray image which was xerographically copiable.

C. The acetic anhydride filtrate from part B of this example was treated first with dilute hydrochloric acid (16 g. of concentrated acid plus 80 g. of water), then basified, affording 3-(2,4-bis(dimethylamino)phenyl)-3-(4-(dimethylamino)phenyl)-6-(dimethylamino)phthalide (I: $X = Y^4 = Z^6 = (CH_3)_2N$, $Y^2 = Z^4 = Z^5 = Z^7 = H$) (m.p. 182°–185° C. after purification).

When applied to acidic clay 3-(2,4-bis(dimethylamino)phenyl)-3-(4-(dimethylamino)phenyl)-6-(dimethylamino)phthalide rapidly formed a violet-purple image which was xerographically copiable.

D. Propionic anhydride, phosphorus oxychloride or thionyl chloride can be substituted for acetic anhydride in part B of this example.

EXAMPLE 13

A. In a manner similar to that of part A of Example 3 condensation of 4-(dimethylamino)phthalic anhydride (1.91 g.) and N,N,N',N'-tetramethyl-m-phenylenediamine (1.64 g.) in contact with zinc chloride (2.70 g.) and with chlorobenzene (50 ml.) as diluent afforded 2-(2,4-bis(dimethylamino)benzoyl)-4-(dimethylamino)benzoic acid (II: $Y'^2 = Y'^4 = Z'^5 = (CH_3)_2N$, $Z^4 = Z'^6 = Z^7 = H$) (m.p. 216°–222° C.) or the 5-(dimethylamino) isomer thereof.

B. In a manner similar to that of part B of Example 3 condensation of 2-(2,4-bis(dimethylamino)benzoyl)-4-(dimethylamino)benzoic acid or the 5-(dimethylamino) isomer thereof (10 g.) and N,N,N',N'-tetramethyl-m-phenylenediamine (2.30 g.) and crystallization of the product from toluene afforded 3,3-bis(2,4-bis(dimethylamino)phenyl)-5-(dimethylamino)phthalide (I: $X = Y^2 = Y^4 = Z^5 = (CH_3)_2N$, $Z^4 = Z^6 = Z^7 = H$) (m.p. 188°–192° C.) or the 6-(dimethylamino) isomer thereof.

C. Substituting N-ethyl-N-(4-hydroxybutyl)aniline for N,N,N',N'-tetramethyl-m-phenylenediamine in part B of this example and deacetylating the resulting product, there is obtained 3-(2,4-bis(dimethylamino)phenyl)-3-(4-(ethyl(4-hydroxybutyl)amino)phenyl)-5-(dimethylamino)phthalide (I: $X = Z^5 = (CH_3)_2N$, $Y^2 = Z^4 = Z^6 = Z^7 = H$, $Y^4 = CH_3CH_2(HO(CH_2)_4)N$) or the 6-(dimethylamino) isomer thereof.

D. Substituting 4-methylphthalic anhydride, 4-nitrophthalic anhydride or 4-chlorophthalic anhydride for 4-(dimethylamino)phthalic anhydride in part A of this example, there are obtained, respectively, 2-(2,4-bis(dimethylamino)benzoyl)-5-methylbenzoic acid (VI: $X = (CH_3)_2N$, $Z^4 = Z'''^5 = Z^7 = H$, $Z'''^6 = CH_3$), 2-(2,4-bis(dimethylamino)benzoyl)-5-nitrobenzoic acid (VI: $X = (CH_3)_2N$, $Z^4 = Z'^5 = Z^7 = H$, $Z'^6 = O_2N$) and 2-(2,4-bis(dimethylamino)benzoyl)-5-chlorobenzoic acid (VI: $X = (CH_3)_2N$, $Z^4 = Z'^5 = Z^7 = H$, $Z'^6 = Cl$).

E. Substituting 2-(2,4-bis(dimethylamino)benzoyl)-5-methylbenzoic acid, 2-(2,4-bis(dimethylamino)benzoyl)-5-nitrobenzoic acid or 2-(2,4-bis(dimethylamino)benzoyl)-5-chlorobenzoic acid for 2-(2,4-bis(dimethylamino)benzoyl)-5-(dimethylamino)benzoic acid in part B of this example, there are obtained, respectively, 3,3-bis(2,4-bis(dimethylamino)phenyl)-6-methylphthalide (I: $X = Y^2 = Y^4 = (CH_3)_2N$, $Z^4 = Z^5 = Z^7 = H$, $Z^6 = CH_3$), 3,3-bis(2,4-bis(dimethylamino)phenyl)-6-nitrophthalide (I: $X = Y^2 = Y^4 = (CH_3)_2N$, $Z^4 = Z^5 = Z^7 = H$, $Z^6 = O_2N$) and 3,3-bis(2,4-bis(dimethylamino)- phenyl)-6-chlorophthalide (I: $X = Y^2 = Y^4 = (CH_3)_2N$, $Z^4 = Z^5 = Z^7 = H$, $Z^6 = Cl$).

EXAMPLE 14

Sodium nitrite is added to a mixture of 3,3-bis(2,4-bis(dimethylamino)phenyl)-6-aminophthalide in dilute hydrobromic acid. The resulting mixture is added to a solution of cuprous bromide in dilute hydrobromic acid, affording, after basification, 3,3-bis(2,4-bis(dimethylaminophenyl)-6-bromophthalide (I: $X = Y^2 = Y^4 = (CH_3)_2N$, $Z^4 = Z^5 = Z^7 = H$, $Z^6 = Br$).

What is claimed is:
1. 2-(2,4-Bis(dimethylamino)benzoyl)-3,4,5,6-tetrachlorobenzoic acid.
2. 2-(2,4-Bis(dimethylamino)benzoyl-4-(dimethylamino)benzoic acid.
3. 2-(2,4-Bis(dimethylamino)benzoyl)-5-(dimethylamino)benzoic acid.

* * * * *